(12) United States Patent
Zavatsky

(10) Patent No.: US 9,468,432 B2
(45) Date of Patent: Oct. 18, 2016

(54) MEDICAL INSTRUMENT WITH SUCTION

(71) Applicant: Joseph Michael Zavatsky, New Orleans, LA (US)

(72) Inventor: Joseph Michael Zavatsky, New Orleans, LA (US)

(*) Notice: Subject to any disclaimer, the term of this patent is extended or adjusted under 35 U.S.C. 154(b) by 332 days.

(21) Appl. No.: 14/032,707

(22) Filed: Sep. 20, 2013

(65) Prior Publication Data

US 2014/0081307 A1    Mar. 20, 2014

Related U.S. Application Data

(60) Provisional application No. 61/703,309, filed on Sep. 20, 2012.

(51) Int. Cl.
    *A61B 17/02*    (2006.01)
    *A61B 17/32*    (2006.01)

(52) U.S. Cl.
    CPC ............ *A61B 17/0218* (2013.01); *A61B 2017/320044* (2013.01); *A61B 2217/005* (2013.01)

(58) Field of Classification Search
    CPC .......... A61B 17/02; A61B 17/0281; A61B 2017/0237; A61B 2017/0243; A61B 2018/00291; A61B 1/00094; A61M 1/0058; A61M 1/0086
    See application file for complete search history.

(56) References Cited

U.S. PATENT DOCUMENTS

| | | |
|---|---|---|
| 4,049,000 A | 9/1977 | Williams |
| 4,126,127 A | 11/1978 | May |
| 5,159,921 A | 11/1992 | Hoover |
| 5,755,660 A | 5/1998 | Tyagi |
| 5,897,489 A | 4/1999 | Urbanowicz et al. |
| 6,033,362 A | 3/2000 | Cohn |
| 6,152,886 A | 11/2000 | Phelan |
| 6,241,658 B1 | 6/2001 | Goodrich |
| 6,248,061 B1 | 6/2001 | Cook, Jr. |
| 6,656,109 B2 | 12/2003 | DeVries et al. |
| 6,764,444 B2 | 7/2004 | Wu et al. |
| 6,875,173 B2 | 4/2005 | Suddaby |
| 7,226,413 B2 | 6/2007 | McKinley |
| 7,338,440 B1 | 3/2008 | Smith |
| 8,206,295 B2 | 6/2012 | Kaul |
| 8,221,316 B2 | 7/2012 | DeGould |
| 2005/0065496 A1* | 3/2005 | Simon et al. .......... 604/500 |
| 2007/0093694 A1 | 4/2007 | Fassuliotis et al. |
| 2007/0179343 A1* | 8/2007 | Shelokov ........ A61B 17/02 600/205 |
| 2012/0078059 A1* | 3/2012 | Perez-Cruet ...... A61B 17/0218 600/210 |

FOREIGN PATENT DOCUMENTS

| | | |
|---|---|---|
| CN | 2787148 | 6/2006 |
| GB | 2116043 | 9/1983 |
| RU | 2185110 | 7/2002 |

* cited by examiner

*Primary Examiner* — Eduardo C Robert
*Assistant Examiner* — Julianna N Harvey
(74) *Attorney, Agent, or Firm* — Adam and Reese LLP

(57) ABSTRACT

Surgical instruments for dissection and retraction, providing suction to remove fluids, smoke and debris at the site of a surgical procedure. A surgical dissector/retractor having a handle and head with a suction channel passing within the dissector/retractor. The dissector/retractor includes a smooth leading edge and a suction port on a top surface of the head.

18 Claims, 6 Drawing Sheets

MEDICAL INSTRUMENT WITH SUCTION

CROSS REFERENCE TO RELATED APPLICATIONS

This application claims priority to Provisional Patent Application 61/703,309 filed Sep. 20, 2012.

FIELD OF INVENTION

The present invention relates generally to medical instruments and, in a particular though non-limiting embodiment, to a medical instrument with suction for use during surgery that can remove fluids, debris, smoke and other matter from a surgical field.

BACKGROUND

In various medical procedures, instruments are utilized to manipulate tissues during the procedure. A surgical instrument is a tool or device designed for performing a specific action or carrying out desired effects during a surgery or operation, such a manipulating tissue or providing access for viewing or for other instruments.

For example, during surgical procedures it is often necessary to retract tissue. A retractor is a surgical instrument by which a surgeon can either actively separate the edges of a surgical incision or wound, or can hold back underlying organs and tissues, so that body parts under the incision may be accessed and visualized. A surgeon may manipulate a retractor in one hand while operating another instrument, such as scalpel or other surgical instrument, in the other hand.

In addition to needing to retract tissues for access to underlying organs or tissues, the surgical site often has a significant amount of fluid (e.g. blood, pus, or cerebrospinal fluid) which can obscure the surgeon's view of the underlying organs and/or tissues. In order to address this concern, suction may be applied to remove the fluid and clear the surgical site. Unfortunately, under current technologies, the suction must be obtained from a third instrument. This limitation either requires the surgeon to put down one of the two instruments already in the surgeon's hands to apply suction or the presence of a medical assistant to operate the suction instrument in the surgical field. Because of the limited and crowded nature of a surgical site, especially during minimally invasive surgery or in small surgical sites, having a medical assistant manipulating instruments in the surgical site can be cumbersome and potentially harmful.

There is, therefore, a long-standing, but unmet need for a surgical instrument that overcomes the deficiencies in the prior art and provides for an effective way to dissect and retract tissue and simultaneously suction the surgical site to provide a clear and safe operative field.

SUMMARY

In exemplary embodiments of the present invention, a surgical dissector/retractor with suction is provided, having: a handle; an intermediate section; a head comprising a top surface, bottom surface, side edges and a leading edge; and a suction channel having at least one suction port and attached to a suction connector. The suction connector is located at a first end of the handle. The intermediate section is attached to a second end of the handle and attaches to the head. The suction channel passes within an interior surface of the handle, intermediate section, and head, opening at the at least one suction port. The at least one suction port is on the top surface of the head. The leading edge of the head is smooth. The suction connector is configured to attach to a vacuum.

The top surface of the head may be slightly concave. The handle may be one of straight and bayoneted. The at least one suction port may be located approximately in a mid-portion of the top surface of the head. The at least one suction port may be proximal to the intermediate section. The at least one suction port may be distal to the intermediate section. The surgical dissector/retractor may have at least two suction ports. The surgical dissector/retractor may be stainless steel. The surgical dissector/retractor may be plastic. A width of the intermediate section may be narrower than a distance between the side edges of the head. A width of the intermediate section may be wider than a distance between the top surface and the bottom surface of the head.

In exemplary embodiments of the present invention a surgical instrument is provided, having: an elongate body comprising a handle and a head; a suction channel passing within the elongate body and configured to receive a vacuum at a first end of the handle; and at least one suction port on a top surface of the head. The head comprises the top surface, a bottom surface and a leading edge. The leading edge is smooth.

The top surface of the head may be slightly concave. The leading edge may be one of straight and rounded. The handle may be one of straight and bayoneted. The surgical instrument may have an intermediate section connecting the handle and the head. The at least one suction port may be located approximately in a mid-portion of the top surface of the head. The at least one suction port may be proximal to the handle. The at least one suction port may be distal to the handle. The surgical retractor may be stainless steel. The surgical retractor may be plastic.

DESCRIPTION

Figure 7:
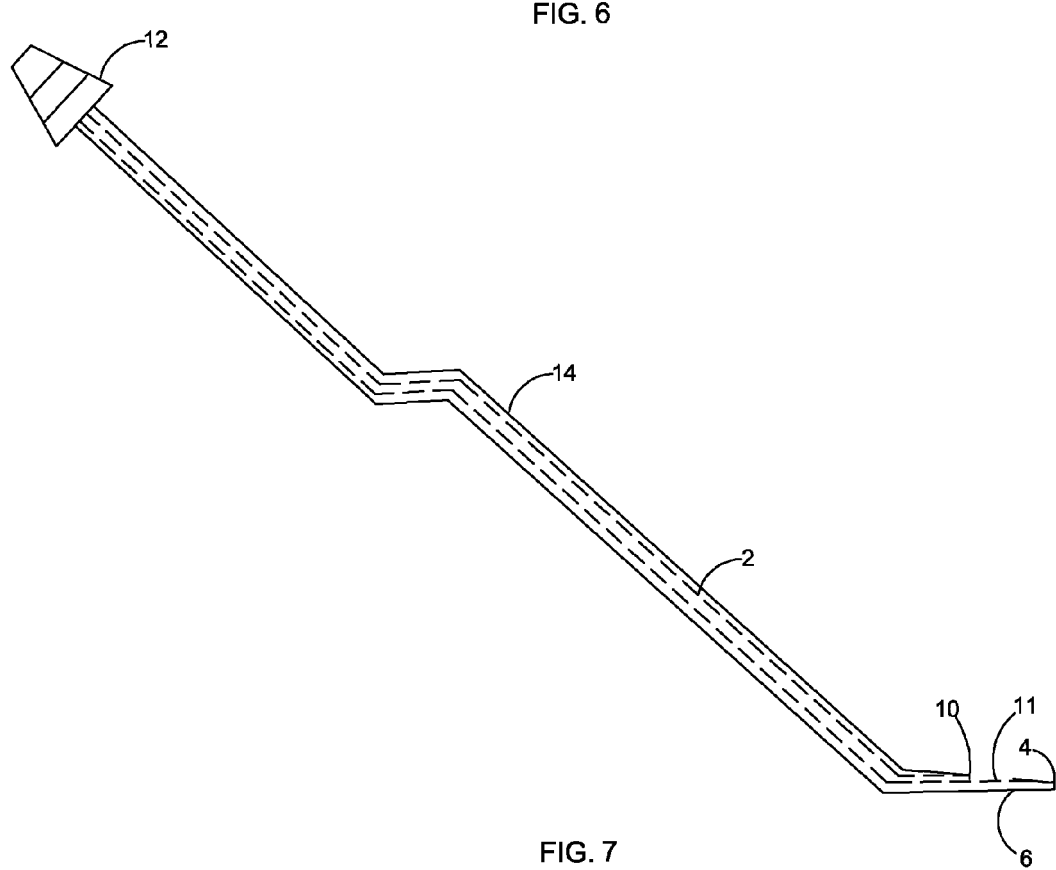
FIG. 7 illustrates a bayonetted configuration for a medical instrument according to example embodiments.

In an example embodiment, a retraction medical instrument is provided having suction capabilities. The medical instrument may be utilized to remove fluids and other matter from a surgical site while dissecting and retracting tissues and/other matter. In certain embodiments, the instrument includes a blunt/smooth tip that dissects tissue and then functions as a retractor at an end of the elongated instrument. In example embodiments, the instrument has an elongated body, which may be straight or bayoneted, with a suction channel passing within the length of the elongated body and opening at a suction port at a head of the elongated body. The elongated body may be substantially straight as shown in FIGS. 1 to 4 or bayoneted, as shown in FIG. 7, to allow better visualization in smaller operative surgical sites. The suction port is in communication with the vacuum channel and is in incorporated into the dissector/retractor end, which is also configured to suction and remove fluid, smoke, and/or other debris from a surgical site. In still other embodiments, at an end opposite the retractor, the instrument includes a suction connector in communication with the vacuum channel. The suction connector is configured to connect to a vacuum system such that suction pressure is applied through the vacuum channel to the suction port.

Figure 1:
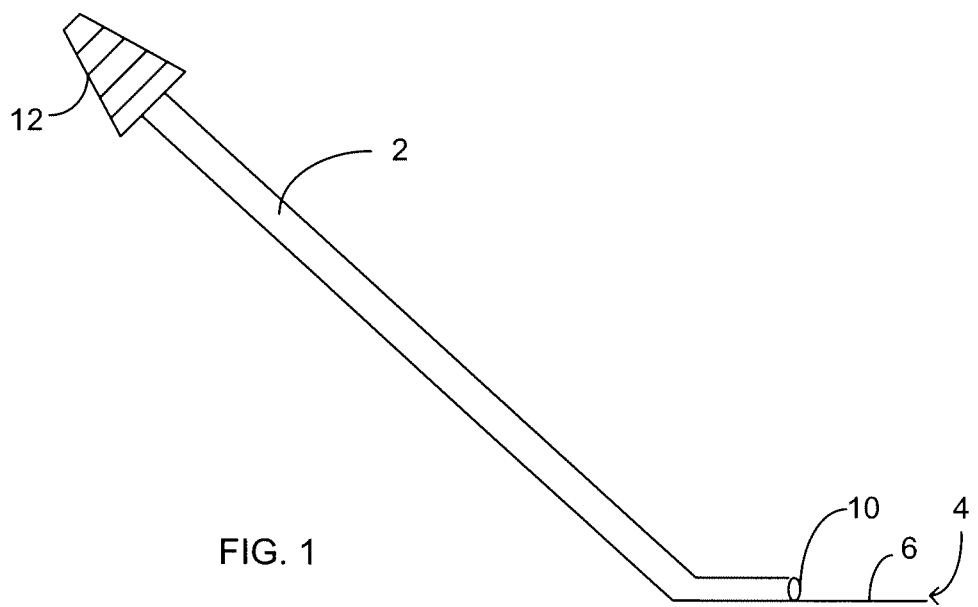
FIG. 1 illustrates a side view of a medical instrument showing a vacuum channel according to example embodiments.

In the example embodiment shown in FIG. 1, the medical instrument comprises a head 6 with leading edge 4 and vacuum channel 2 in communication with suction connector 12. The vacuum channel opens at suction port 10 which is located on a top surface of the head 6. The suction port 10 is an opening of the vacuum channel and can be utilized to suction fluid, smoke, and/or debris from a medical site such as a surgical opening. The leading edge 4 and head 6 may be used to dissect and retract tissues, such as nerves, the spinal cord or thecal sac, muscle, organs, etc. to allow access to underlying tissues.

Figure 2:
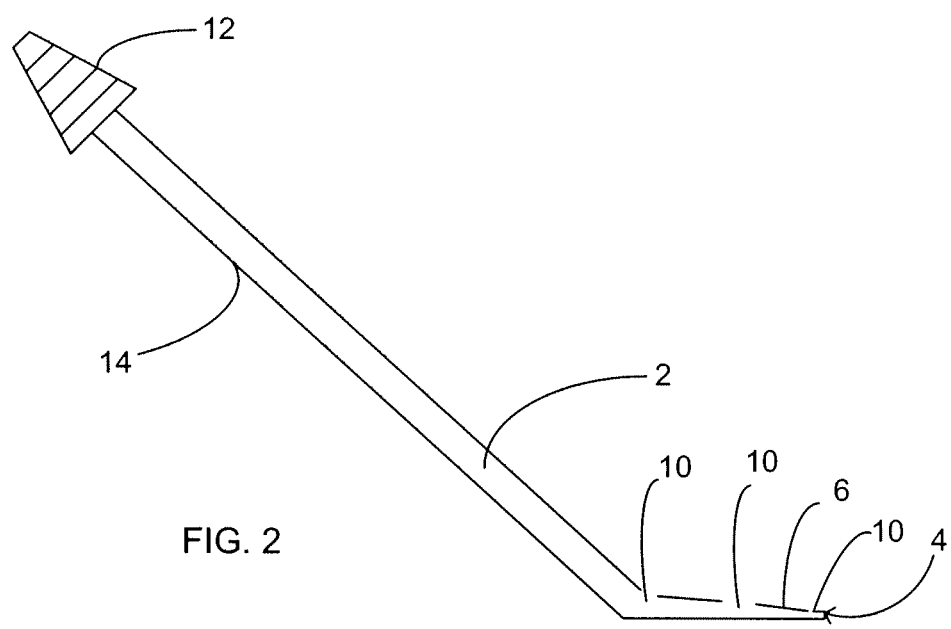
FIG. 2 illustrates a side view of a medical instrument according to example embodiments.

In the example embodiment shown in FIG. 2, the medical instrument includes a handle 14 with the vacuum channel passing within the handle. In certain embodiments, the head 6 may be slightly concave 11 (see FIG. 6). Leading edge 4 is smooth and may be rounded. Suction connector 12 is located at a first end of handle 14, opposite a second end of handle 14 which connects to head 6. FIG. 2 shows multiple optional locations for suction port 10. Suction port 10 may be located at or near leading edge 4, proximal to handle 14, or at any point between. See also, FIGS. 5 to 5B. Multiple suction ports 10 may be included at multiple locations.

Figure 3:
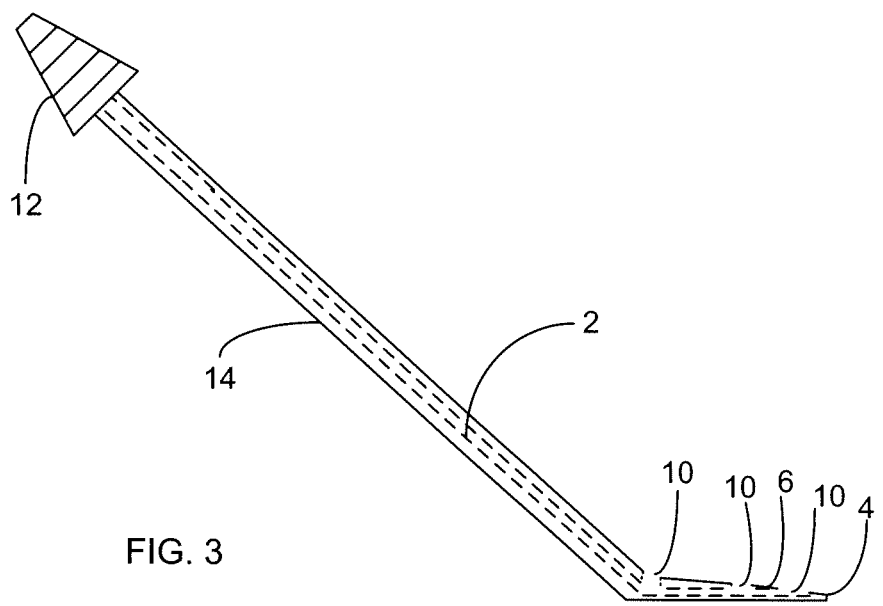
FIG. 3 illustrates a side view of a medical instrument showing a vacuum channel inside an elongated body according to example embodiments.

The example embodiment in FIG. 3 shows the vacuum channel passing within the handle 14. The vacuum channel passes from suction port 10 to suction connector 12 such that connection of a vacuum system to the suction connector 12 will cause suction force at suction port 10, allowing removal of fluids, smoke and debris at or near head 6. As shown, suction port 10 may be located centrally on a top surface of head 6, near or within leading edge 4, proximal to handle 14, or somewhere in between. See, e.g., FIGS. 5 to 5B. Multiple suction ports 10 may be incorporated.

Figure 4:
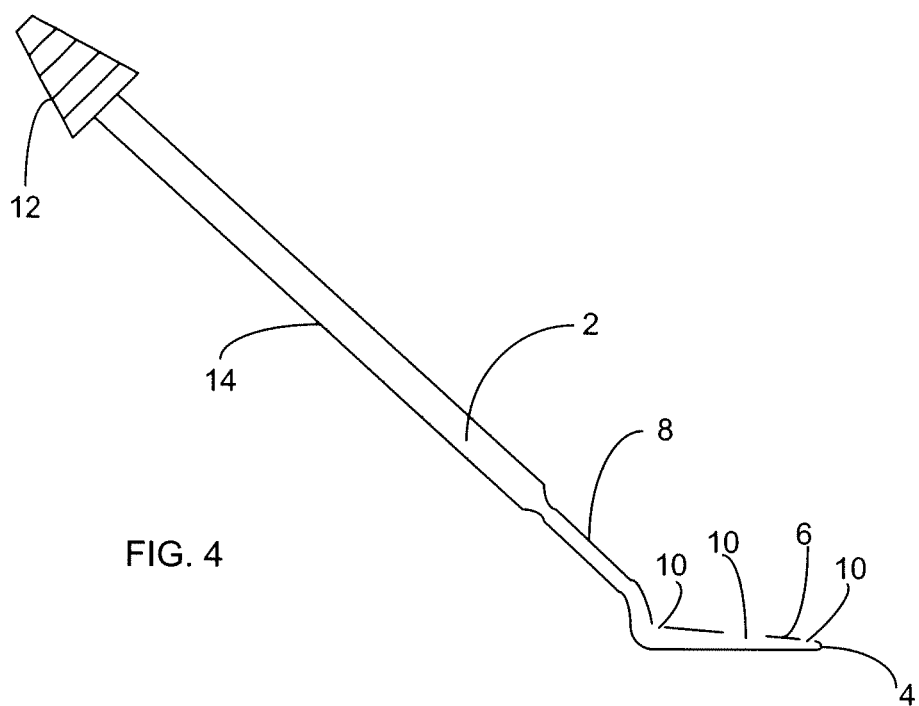
FIG. 4 illustrates a side view of medical instrument according to example embodiments.

In the example embodiment shown in FIG. 4, an intermediate section 8 is located between head 6 and handle 14. Handle 14 may be straight as shown in FIGS. 2 to 4 or bayoneted as shown in FIG. 7. In an example embodiment, the intermediate section 8 is thinner than handle 14 and tapers into head 6. In certain embodiments incorporating an intermediate section, vacuum channel 2 passes from handle 14, through intermediate section 8, and into head 6. As shown, vacuum channel 2 may open at suction port 10, which may be located at a base of intermediate section 8 or further down on the top surface of head 6. Head 6 may be substantially flat, having a top surface, a bottom surface, and two side edges 16. See, e.g., FIG. 5.

Figure 5:
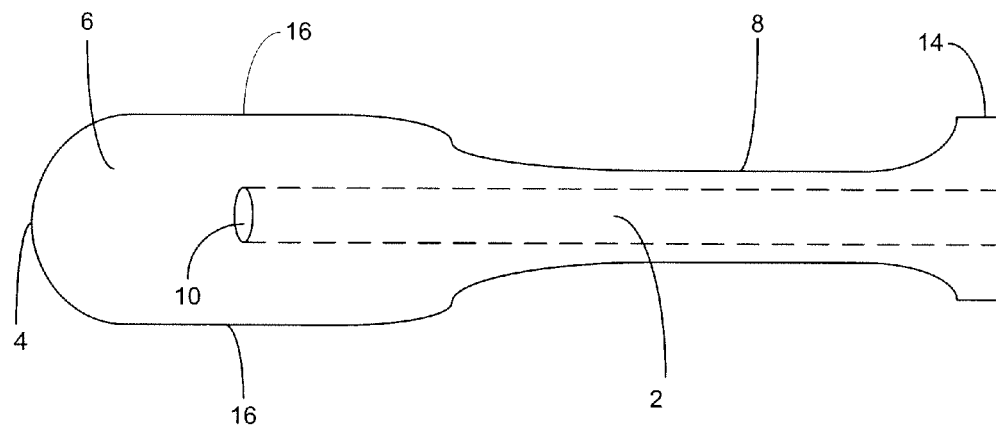
FIG. 5 illustrates a top view of a head portion of a medical instrument according to example embodiments.
Figure 5A:
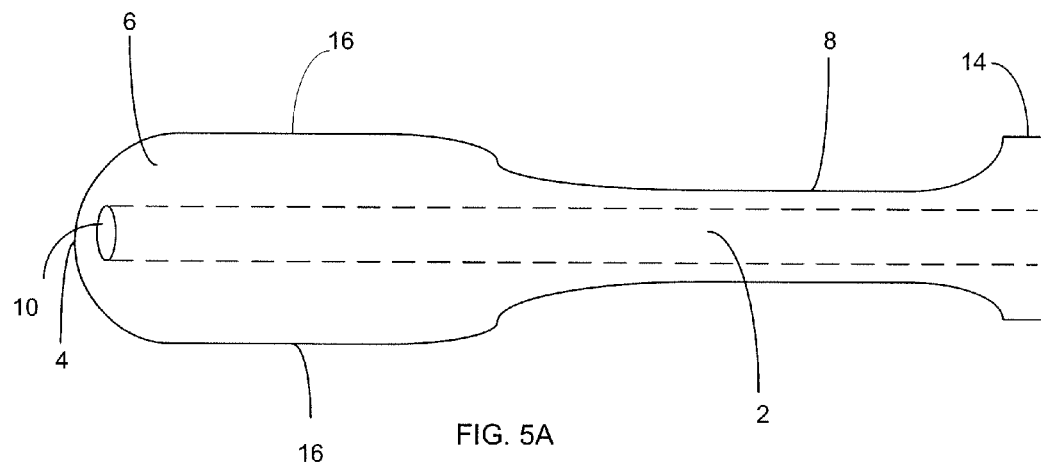
FIG. 5A illustrates a top view of a head portion of a medical instrument according to example embodiments.
Figure 5B:
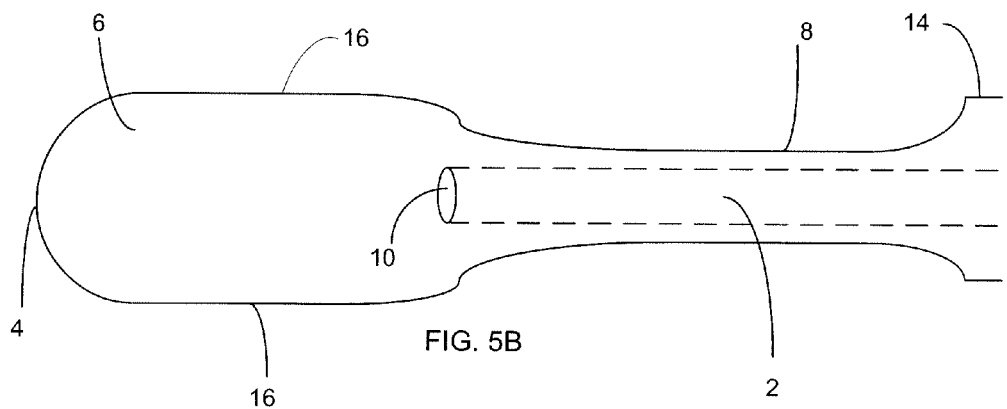
FIG. 5B illustrates a top view of a head portion of a medical instrument according to example embodiments.
Figure 6:
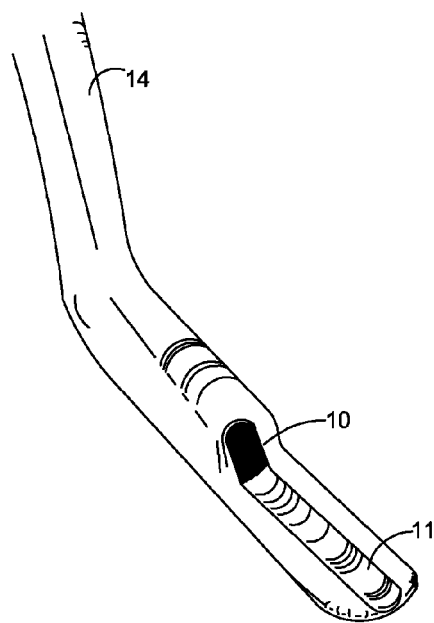
FIG. 6 illustrates a top surface of the head being slightly concave for a medical instrument according to example embodiments.

In the embodiment shown in FIG. 5, an example head section is illustrated having a leading edge 4 and side edges 16. Head 6 is relatively thin and a top surface of head 6 may be slightly concave 11 (see FIG. 6). A width of intermediate section 8 may be narrower than a distance between side edges 16 of the head 6 and may be wider than a distance between the top surface and bottom surface of head 6. In certain embodiments, suction port 10, which is an opening of the vacuum channel, is located generally centrally on the top portion of the head 6. In other embodiments, suction port 10 is located at a distal end of intermediate section 8 or at a distal end of head 6. See, e.g., FIGS. 5A and 5B. Embodiments may include two or more suction ports 10 at various locations. In FIG. 5, the vacuum channel can be viewed as dotted lines passing through the intermediate section 8 and into the handle 14. Although the leading edge 4 is rounded in FIG. 5, various embodiments are possible, including rounded, flat, curved and/or tapered. Leading edge 4 is a smooth surface. Embodiments of the present invention may be used for dissection and retraction of neural tissue, including nerves, thecal sac, and spinal cord in both open and minimally invasive spine procedures. The side edges 16 can be flat or curved and the length of the side edges can be modified for the medical application. In still other embodiments, the suction port 10 may be located distally towards the leading edge or proximally toward the intermediate section (or handle).

Embodiments of the medical instrument may be made of rigid, durable material, such as stainless steel other metal. In other embodiments, the medical instrument may be made of disposable materials such as plastic or other suitable material. In an example embodiment, the suction connector may be connected to a vacuum system using an elastic tube releasably and functionally communicating with the suction connector. In still other embodiments, the medical instrument includes a switch located on the handle configured to control the application of suction force through the vacuum channel such that suction at the suction port may be turned on or off.

The foregoing specification is providing only for illustrative purposes, and is not intended to describe all possible aspects of the present invention. While the invention has herein been shown and described in detail with respect to several exemplary embodiments, those of ordinary skill in the art will appreciate that minor changes to the description, and various other modifications, omissions and additions may also be made without departing from the spirit or scope thereof.

What is claimed is:

1. A surgical dissector/retractor with suction for use in retracting, dissecting and suctioning tissue of a patient, comprising:
   a handle;
   an intermediate section;
   a head comprising a top surface, bottom surface, side edges and a leading edge, the bottom surface of the head being substantially flat when viewed from a side view so as to be configured for use in dissection of tissue; and
   a suction channel having a suction port and attached to a suction connector;
   wherein the suction connector is located at a first end of the handle;
   wherein the intermediate section is attached to a second end of the handle and attaches to the head;
   wherein the suction channel passes within an interior surface of the handle, intermediate section, and head, the channel opening at the suction port;
   wherein the suction port is on the top surface of the head, the head angled relative to the handle such that the handle is closer to the suction port and the top surface of the head than to the bottom surface of the head;

wherein the leading edge of the head is rounded to further configure the head for use in dissection of tissue;

wherein the top surface of the head is slightly concave to thereby form a single open channel on the head, the open channel extending from the at least one suction port to the leading edge of the head such that the open channel is in fluid communication with the suction channel for use in suctioning fluid from said patient during dissection; and wherein the suction connector is configured to attach to a vacuum.

2. The surgical dissector/retractor of claim 1, wherein the handle is one of straight and bayoneted.

3. The surgical dissector/retractor of claim 1, wherein the suction port is located approximately in a mid-portion of the top surface of the head.

4. The surgical dissector/retractor of claim 1, wherein the suction port is proximal to the intermediate section.

5. The surgical dissector/retractor of claim 1, wherein the suction port is distal to the intermediate section.

6. The surgical dissector/retractor of claim 1, further comprising: a second suction port, the second suction port formed in the suction channel in the head and intermediate to the proximal end of the head and the suction port.

7. The surgical dissector/retractor of claim 1, wherein the surgical dissector/retractor is stainless steel and a width of the handle is substantially uniform throughout a length of the handle and the intermediate section.

8. The surgical dissector/retractor of claim 1, wherein the surgical dissector/retractor is plastic.

9. The surgical dissector/retractor of claim 1, wherein a width of the intermediate section is narrower than a distance between the side edges of the head.

10. The surgical dissector/retractor of claim 1, wherein a width of the intermediate section is wider than a distance between the top surface and the bottom surface of the head.

11. A surgical instrument for use in retracting, dissecting and suctioning tissue of a patient, comprising:

an elongate body comprising a handle and a head;

a suction channel passing within the elongate body, a proximal end of the suction channel configured to receive a vacuum at a first end of the handle;

a distal end of the suction channel terminating in a suction port, the suction port located on a top surface of the head;

wherein the head comprises the top surface, a bottom surface and a leading edge, the bottom surface being substantially flat when viewed from a side view so as to be configured for use in dissection of tissue, the head angled relative to the handle such that the handle is closer to the suction port and the top surface of the head than to the bottom surface of the head;

wherein the top surface of the head is slightly concave to thereby form a single open channel on the head, the open channel extending from the at least one suction port to the leading edge of the head such that the open channel is in fluid communication with the suction channel for use in suctioning fluid from said patient during dissection; and wherein the leading edge is rounded to further configure the head for use in dissection of tissue.

12. The surgical instrument of claim 11, wherein the handle is one of straight and bayoneted.

13. The surgical instrument of claim 11, further comprising: an intermediate section connecting the handle and the head.

14. The surgical retractor of claim 11, wherein the suction port is located approximately in a mid-portion of the top surface of the head.

15. The surgical retractor of claim 11, wherein the suction port is proximal to the handle.

16. The surgical retractor of claim 11, wherein the suction port is distal to the handle.

17. The surgical retractor of claim 11, wherein the surgical retractor is stainless steel and a width of the handle is substantially uniform throughout a length of the handle and the intermediate section.

18. The surgical retractor of claim 11, wherein the surgical retractor is plastic.

* * * * *